(12) United States Patent
Prstojevich

(10) Patent No.: US 10,729,936 B2
(45) Date of Patent: Aug. 4, 2020

(54) MULTI-MODE ACCELERATION-BASED ATHLETICISM MEASUREMENT SYSTEM

(71) Applicant: NIKE Inc., Beaverton, OR (US)

(72) Inventor: Michael Prstojevich, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 200 days.

(21) Appl. No.: 14/845,599

(22) Filed: Sep. 4, 2015

(65) Prior Publication Data
US 2015/0375043 A1 Dec. 31, 2015

Related U.S. Application Data

(63) Continuation of application No. 14/273,585, filed on May 9, 2014, now Pat. No. 9,126,070, which is a (Continued)

(51) Int. Cl.
*G09B 19/00* (2006.01)
*A63B 24/00* (2006.01)
(Continued)

(52) U.S. Cl.
CPC .......... *A63B 24/0062* (2013.01); *A61B 5/112* (2013.01); *A61B 5/1123* (2013.01);
(Continued)

(58) Field of Classification Search
CPC . A61B 5/1125; A61B 5/1123; A63B 24/0062; G09B 19/0038
See application file for complete search history.

(56) References Cited

U.S. PATENT DOCUMENTS 1,020,005 A 3/1912 Witthoefft
3,492,582 A 1/1970 Heywood
(Continued)

FOREIGN PATENT DOCUMENTS

WO 2006053000 A2 5/2006

OTHER PUBLICATIONS

Ermes et al. "Detection of Daily Activities and Sports With Wearable Sensors in Controlled and Uncontrolled Conditions." IEEE Transactions on Information Technology in Biomedicine, vol. 12, No. 1, Jan. 2008.*
(Continued)

*Primary Examiner* — Robert J Utama
(74) *Attorney, Agent, or Firm* — Banner & Witcoff, Ltd.

(57) ABSTRACT

A multi-mode athleticism movement measurement system includes an athlete-borne acceleration sensor and an athleticism processing device to determine athleticism information based upon one or more timing measurements from the athlete-borne acceleration sensor, the athleticism information corresponding to any of multiple athleticism measurement modes available on athleticism processing device and selectable by a user. A data link between the athlete-borne acceleration sensor and the athleticism rating processing device transmits the one or more timing measurements from the athlete-borne acceleration sensor to the athleticism rating processing device.

20 Claims, 5 Drawing Sheets

Related U.S. Application Data continuation of application No. 13/709,658, filed on Dec. 10, 2012, now Pat. No. 8,721,342, which is a continuation of application No. 13/358,166, filed on Jan. 25, 2012, now Pat. No. 8,337,212, which is a continuation of application No. 11/864,438, filed on Sep. 28, 2007, now Pat. No. 8,128,410.

(60) Provisional application No. 60/848,271, filed on Sep. 29, 2006.

(51) Int. Cl.
| | | |
|---|---|---|
| *A61B 5/11* | (2006.01) | |
| *G01P 15/00* | (2006.01) | |
| *A63B 71/06* | (2006.01) | |
| *A63B 23/04* | (2006.01) | |
| *A63B 69/00* | (2006.01) | |

(52) U.S. Cl.
CPC .............. *A63B 24/00* (2013.01); *A63B 71/06* (2013.01); *G01P 15/00* (2013.01); *A61B 2503/10* (2013.01); *A61B 2562/0219* (2013.01); *A63B 23/0458* (2013.01); *A63B 24/0075* (2013.01); *A63B 69/0028* (2013.01); *A63B 71/0686* (2013.01); *A63B 2024/0065* (2013.01); *A63B 2024/0078* (2013.01); *A63B 2071/0625* (2013.01); *A63B 2220/17* (2013.01); *A63B 2220/40* (2013.01); *A63B 2220/803* (2013.01); *A63B 2220/836* (2013.01); *A63B 2225/20* (2013.01); *A63B 2225/50* (2013.01); *G09B 19/0038* (2013.01)

(56) References Cited

U.S. PATENT DOCUMENTS

| | | | |
|---|---|---|---|
| 3,797,010 A | 3/1974 | Adler et al. | |
| 4,771,394 A * | 9/1988 | Cavanagh | A43B 3/0005 235/105 |
| 4,978,303 A | 12/1990 | Lampbell | |
| 5,149,084 A | 9/1992 | Dalebout et al. | |
| 5,197,489 A * | 3/1993 | Conlan | A61B 5/11 600/484 |
| 5,300,921 A | 4/1994 | Hoch et al. | |
| 5,524,637 A | 6/1996 | Erickson | |
| 5,613,924 A | 3/1997 | Lee | |
| 5,737,280 A | 4/1998 | Kokubo | |
| 5,788,618 A * | 8/1998 | Joutras | A43B 1/0054 482/114 |
| 5,916,063 A | 6/1999 | Alessandri | |
| 5,937,387 A | 8/1999 | Summerell et al. | |
| 5,944,633 A | 8/1999 | Wittrock | |
| 5,976,083 A | 11/1999 | Richardson et al. | |
| 6,013,007 A | 1/2000 | Root et al. | |
| 6,132,337 A | 10/2000 | Krupka et al. | |
| 6,176,837 B1 * | 1/2001 | Foxlin | G01C 21/165 128/897 |
| 6,231,481 B1 | 5/2001 | Brock | |
| 6,292,792 B1 | 9/2001 | Baffes et al. | |
| 6,356,856 B1 | 3/2002 | Damen et al. | |
| 6,449,583 B1 | 9/2002 | Sakumoto et al. | |
| 6,450,922 B1 | 9/2002 | Henderson et al. | |
| 6,458,060 B1 | 10/2002 | Watterson et al. | |
| 6,493,652 B1 | 12/2002 | Ohlenbusch et al. | |
| 6,513,381 B2 * | 2/2003 | Fyfe | A63B 69/0028 702/160 |
| 6,585,622 B1 | 7/2003 | Shum et al. | |
| 6,605,038 B1 | 8/2003 | Teller et al. | |
| 6,710,713 B1 * | 3/2004 | Russo | A63B 24/0021 340/573.1 |
| 6,736,759 B1 | 5/2004 | Stubbs et al. | |
| 6,825,875 B1 | 11/2004 | Strub et al. | |
| 6,837,827 B1 * | 1/2005 | Lee | A63B 24/0084 482/8 |
| 6,876,947 B1 | 4/2005 | Darley et al. | |
| 6,882,955 B1 | 4/2005 | Ohlenbusch et al. | |
| 6,898,550 B1 | 5/2005 | Blackadar et al. | |
| 7,056,265 B1 | 6/2006 | Shea | |
| 7,072,789 B2 | 7/2006 | Vock et al. | |
| 7,081,809 B1 | 7/2006 | Mix et al. | |
| 7,192,387 B2 * | 3/2007 | Mendel | A63B 24/00 434/247 |
| 7,220,220 B2 | 5/2007 | Stubbs et al. | |
| 7,278,966 B2 | 10/2007 | Hjelt et al. | |
| 7,398,151 B1 | 7/2008 | Burrell et al. | |
| 7,503,878 B1 | 3/2009 | Amsbury et al. | |
| 7,519,327 B2 | 4/2009 | White | |
| 7,534,206 B1 | 5/2009 | Lovitt et al. | |
| 7,603,255 B2 * | 10/2009 | Case, Jr. | A63B 24/00 482/4 |
| 7,824,309 B1 | 11/2010 | Tadlock | |
| 8,386,008 B2 * | 2/2013 | Yuen | A61B 5/0002 600/382 |
| 8,460,001 B1 * | 6/2013 | Chuang | G09B 19/0038 434/247 |
| 8,784,274 B1 * | 7/2014 | Chuang | G09B 19/0038 482/9 |
| 2001/0037179 A1 * | 11/2001 | Vock | A42B 3/0433 702/44 |
| 2001/0041647 A1 | 11/2001 | Itoh et al. | |
| 2002/0019296 A1 | 2/2002 | Freeman et al. | |
| 2002/0055857 A1 | 5/2002 | Mault | |
| 2002/0091796 A1 | 7/2002 | Higginson et al. | |
| 2002/0116147 A1 | 8/2002 | Vock et al. | |
| 2003/0163283 A1 | 8/2003 | O'Brien | |
| 2004/0117214 A1 * | 6/2004 | Shea | A63B 24/0062 705/2 |
| 2005/0014113 A1 | 1/2005 | Fleck et al. | |
| 2005/0021110 A1 * | 1/2005 | Maschke | A61B 5/0002 607/88 |
| 2005/0037895 A1 * | 2/2005 | Dugan | G06F 19/3418 482/8 |
| 2005/0107216 A1 * | 5/2005 | Lee | A63B 24/0084 482/8 |
| 2005/0195094 A1 * | 9/2005 | White | A63B 24/0021 340/870.01 |
| 2005/0202934 A1 | 9/2005 | Olrik et al. | |
| 2006/0020177 A1 * | 1/2006 | Seo | A61B 5/222 600/300 |
| 2006/0063980 A1 | 3/2006 | Hwang et al. | |
| 2006/0099556 A1 * | 5/2006 | Yeo | A63B 24/0003 434/247 |
| 2006/0161079 A1 * | 7/2006 | Choi | A61B 5/1117 600/595 |
| 2007/0213126 A1 | 9/2007 | Deutsch et al. | |
| 2007/0272011 A1 * | 11/2007 | Chapa, Jr. | A63B 24/0006 73/379.01 |
| 2008/0090703 A1 | 4/2008 | Rosenberg | |
| 2008/0188354 A1 | 8/2008 | Pauws et al. | |
| 2008/0249736 A1 * | 10/2008 | Prstojevich | A61B 5/112 702/141 |
| 2008/0280730 A1 | 11/2008 | Alexanderson | |
| 2013/0079907 A1 * | 3/2013 | Homsi | A63B 24/00 700/91 |
| 2014/0200834 A1 * | 7/2014 | Ross | A43B 3/0005 702/41 |
| 2015/0186609 A1 * | 7/2015 | Utter, II | A61B 5/0022 600/301 |
| 2015/0257679 A1 * | 9/2015 | Ross | A61B 5/112 702/44 |
| 2016/0196760 A1 * | 7/2016 | Koo | G09B 5/02 434/247 |

OTHER PUBLICATIONS

Math Forum. "Why Take Average in Experiment?" (Year: 2003).*

* cited by examiner

MULTI-MODE ACCELERATION-BASED ATHLETICISM MEASUREMENT SYSTEM

RELATED APPLICATIONS

This application is a continuation of and claims priority from co-pending U.S. non-provisional application Ser. No. 14/273,585, filed May 9, 2014, which is a continuation of U.S. non-provisional application Ser. No. 13/709,658, filed Dec. 10, 2012, now U.S. Pat. No. 8,721,342, which is a continuation of U.S. non-provisional application Ser. No. 13/358,166 filed Jan. 25, 2012, now U.S. Pat. No. 8,337,212, which is a continuation of U.S. non-provisional application Ser. No. 11/864,438 filed Sep. 28, 2007, now U.S. Pat. No. 8,128,410, which claims priority to U.S. provisional application Ser. No. 60/848,271, filed Sep. 29, 2006. The contents of the above referenced applications are hereby incorporated by reference in their entirety.

BACKGROUND AND SUMMARY

Speed, agility, reaction time, and power are some of the determining characteristics influencing the athleticism of an athlete. Athletes strive to improve their athletic performance in these areas, and coaches and recruiters tend to seek those athletes that have the best set of these characteristics for the particular sport.

One method for evaluating and comparing athletes' athleticism involves having the athletes perform a common set of exercises and drills. Athletes that perform the exercises or drills more quickly or more accurately are usually considered to be better than those with slower or less accurate performance for the same exercise or drill. For example, "cone drills" are routinely used in training and evaluating athletes. In a typical "cone drill" the athlete must follow a pre-determined course between several marker cones and, in the process, execute a number of rapid direction changes, and/or switch from forward to backward or lateral running.

Prior systems have utilized accelerometers in or on footwear to discern footsteps or foot strikes of a runner (or walker) and have calculated corresponding running (walking) speed and distance. Examples of such systems are described in U.S. Pat. Nos. 6,513,381, 6,876,947; 6,882,955; 6,898,550, and 7,072,789. However, such accelerometer systems have not been utilized to measure the particular metrics that form the basis of determining broader athleticism ratings.

The present invention includes an athleticism movement measurement system having an athlete-borne movement sensor, such as an accelerometer (e.g., piezoelectric accelerometer), which is borne by an athlete. The athlete-borne acceleration sensor determines timing data for selected athletic drills, and the timing data are delivered to an athleticism rating processing device to determine an athleticism rating based upon the timing data. In one implementation, the timing data are delivered from the sensor to the processing device over a wireless data link.

Additional objects and advantages of the present invention will be apparent from the detailed description of the preferred embodiment thereof, which proceeds with reference to the accompanying drawings.

DETAILED DESCRIPTION

Figure 1:
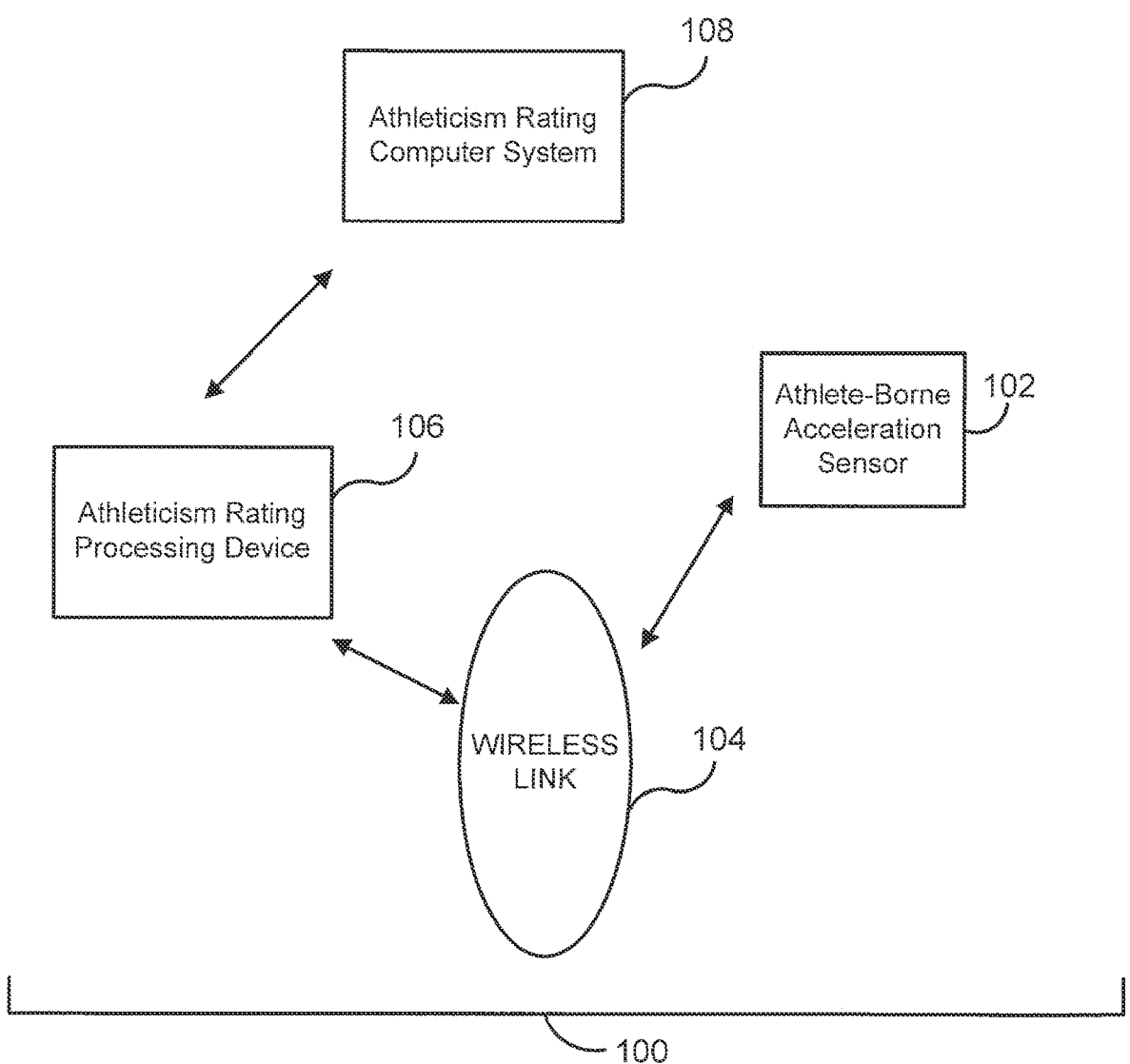
FIG. 1 is a block diagram of an athleticism movement measurement system.

FIG. 1 is a block diagram of a multi-mode acceleration-based athleticism measurement system 100 that includes a movement sensor 102 (e.g., an accelerometer, compression sensor, inertial measurement system, etc.) that is borne by an athlete during different athletic drills or tests to generate acceleration data that are used to generate an athleticism rating, such as a rating described in International patent application no. PCT/US2005/040493 for Athleticism Rating and Performance Measuring Systems, filed by SPARQ, Inc. and incorporated herein by reference. Sensor 12 may include any movement sensor (such as a piezoelectric sensor) that produces voltage or current proportional to acceleration, mechanical stress or strain, etc. For example, a piezoelectric sensor is a highly reliable vibration sensor, accelerometer and dynamic switch element that can detect foot strikes over time to measure athletic performance.

Acceleration sensor 102 may be positioned in a shoe, on top of a shoe, fastened around the ankle or wrist, attached to waist belts or incorporated into apparel on the body of the athlete, or otherwise borne by the athlete. In embodiments described below, an acceleration sensor 102 is positioned in or secured to one or each of an athlete's shoes.

Acceleration sensor 102 communicates over a link 104 with an athleticism rating processing device 106. In one implementation link 104 is a wireless, digital, low-power RF link with 1- or 2-way transmission, but a wired link could alternatively be employed in some applications. Athleticism rating processing device 106 may include one or more of an athleticism timing system, such as a SPARQ XLR8 Digital Timing system, available from SPARQ Marketing & Media of Portland, Oreg., or a stopwatch, sport watch, digital music player (e.g., iPod® media player), cell phone, wireless athleticism measurement kiosk, etc. configured to communicate over link 104 with acceleration sensor 102.

Athleticism rating processing device 106 allows a user (e.g., an athlete, coach, etc.) to select an athleticism measurement mode from among multiple selectable athleticism measurement modes. During a measurement mode, athleticism rating processing device 106 obtains and stores acceleration data from acceleration sensor 102 and selected timing data. In addition, athleticism rating processing device 106 may cue the athlete to perform certain actions during an athleticism measurement or may provide feedback during or after the measurement.

In one implementation, athleticism rating processing device 106 delivers the acceleration data and the timing data by wired or wireless communication to an athleticism rating computer system 108 that calculates an athleticism rating based in part on the acceleration data and timing data. Athleticism rating computer system 108 can be at the location where the athlete performs the athletic drills or tests or may be accessed over a computer network (e.g., the Internet). In an alternative implementation, athleticism rating processing device 106 may calculate an athleticism rating directly.

Figure 2:
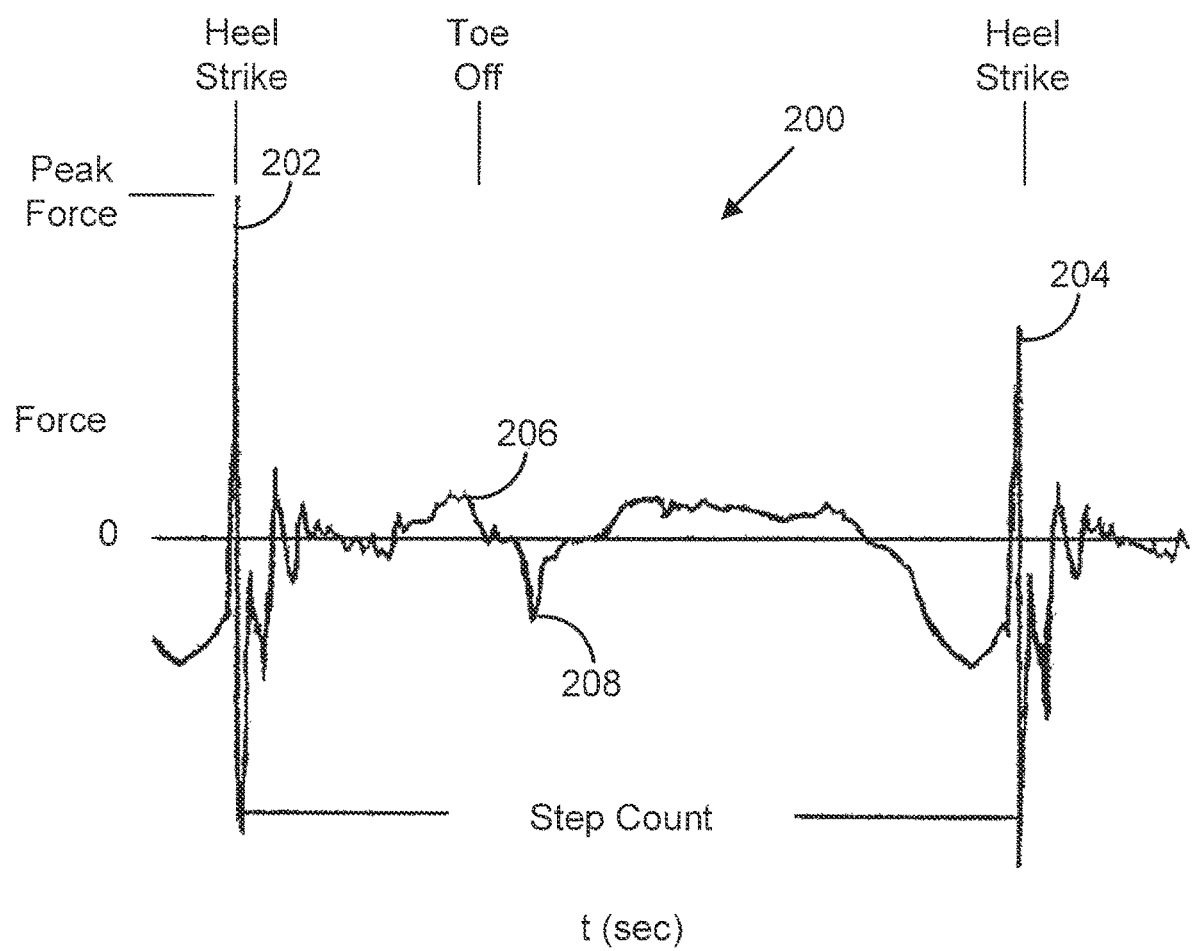
FIG. 2 is a prior art graph of acceleration readings from a shoe-mounted one-dimensional accelerometer during a running stride.

FIG. 2 is graph 200 of prior art acceleration readings from a vertical, one-dimensional shoe-mounted accelerometer during the time period of a running stride to illustrate characteristics of acceleration readings during an athletic activity. Graph 200 includes a first major positive acceleration spike 202 corresponding to a heel strike during a running stride and a second major positive acceleration spike 204 corresponding to a subsequent strike during the running stride. A prolonged secondary positive acceleration peak 206 preceding a negative acceleration spike 208 corresponds to a "toe-off" phase of the running stride.

Prior art acceleration readings form the basis of determining a running or walking speed, as described in U.S. Pat. No. 6,513,381 of Dynastream Innovations, Inc. In contrast, multi-mode acceleration-based athleticism measurement system 100 employs acceleration readings such as that represented by graph 200 in multiple different modes to measure performance in multiple different athletic tests or drills.

As described in International Patent Application No. PCT/US2005/040493, International Publication No. WO 2006/053000 for Athleticism Rating and Performance Measuring Systems, athleticism ratings are calculated from performance results of multiple athletic tests or drills. Multi-mode acceleration-based athleticism measurement system 100 generates acceleration and timing data in multiple distinct modes that correspond to different athletic tests or drills for use in determining an athleticism rating or improving performance in the different tests or drills. Each mode is selectable by an athlete or other user at athleticism rating processing device 106.

For example, multi-mode acceleration-based athleticism measurement system 100 can also be used in drills or tests that characterize agility or "fast feet" by calculating foot contact time or time aloft, such as in ladder and hurdle training drills in which minimization of foot contact time compared to elapsed time is desirable. Foot contact time refers to the time an athlete's foot is in contact with the ground surface, and loft time refers to the time between successive foot contact times during which the athlete's foot is raised above the ground surface. It will be appreciated that "ground surface" refers to any surface or surfaces on which an athlete might act, including athletic fields or tracks or floors, or any other surfaces whether or not specially adapted or designated for athletic performance.

Figure 3:
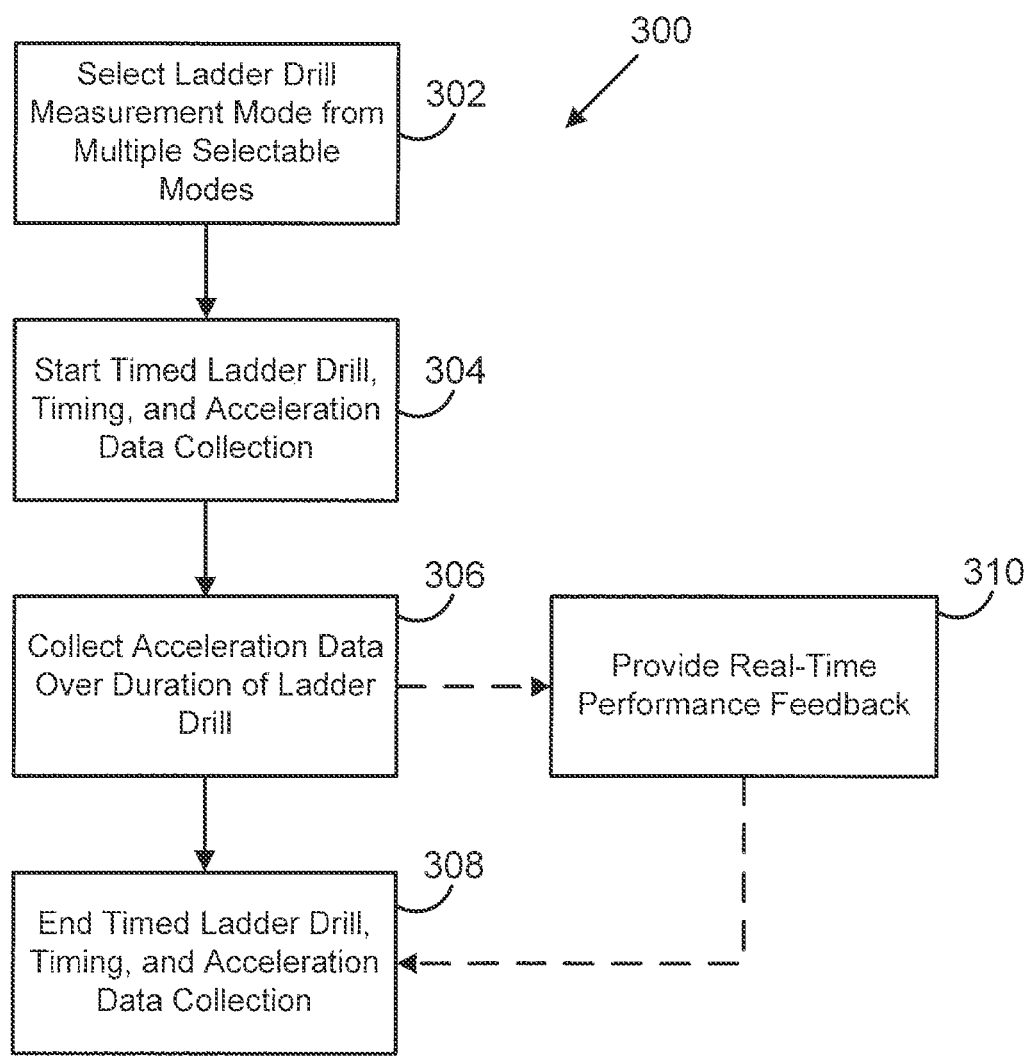
FIG. 3 is a flow diagram of an agility athletic performance measurement method as an illustration of one athleticism measurement mode according to the present invention.

FIG. 3 is a flow diagram of an agility athletic performance measurement method 300 that may be performed during a ladder/hurdle drill may be used in connection with calculating an athletic performance rating or in improving performance in the drill. In a ladder drill, an athlete side steps as quickly as possible into and out of multiple successive regions analogous to spaces between the rungs of a ladder laying flat on the ground. In a hurdle drill, the athlete side moves as quickly as possible over successive hurdles. Conventionally, performance in both types of drill is measured by the overall time in which the athlete completes the drill. Agility athletic performance measurement method 300 may employ an acceleration sensor 102 positioned in or secured to one or each of the athlete's shoes, preferably an acceleration sensor 102 being positioned in or secured to each of the athlete's shoes. The following description refers to a ladder/hurdle drill to indicate the applicability of method 300 to either drill or the like.

In step 302 a ladder/hurdle drill is selected from among multiple selectable drills or exercises, which correspond to different measurement modes, listed on athleticism rating processing device 106 that is worn or carried by the athlete.

In step 304 a timed ladder/hurdle drill is started together with a start of timing of the overall drill duration and a start of collecting of acceleration data by athleticism measurement system 100 in a ladder/hurdle drill mode. The acceleration data may be collected by athleticism rating processing device 106 that is worn, carried, or otherwise borne by the athlete. The start of timing of the overall drill duration may be initiated manually by an observer activating a timer or by the athlete crossing an optical timing start beam, and the start of collecting of acceleration data may be initiated by transmission of a wireless control signal to athleticism rating processing device 106 upon initiation of the overall timing.

In step 306 acceleration data are collected by athleticism measurement system 100 over the duration of the ladder/hurdle drill.

In step 308 the timed ladder/hurdle drill is ended together with timing of the overall drill duration and the collecting of acceleration data by athleticism measurement system 100. The timing of the overall drill duration may be ended manually by an observer de-activating a timer or by the athlete crossing an optical timing end beam, and the collecting of acceleration data may be ended by transmission of a wireless control signal to athleticism rating processing device 106 upon ending of the overall timing.

With an acceleration sensor 102 being positioned in or secured to each of the athlete's shoes, the acceleration data can indicate a ladder/hurdle step frequency or duration for each step in the drill, including distinguishing between the time each foot is on the ground surface and not on the ground surface. A drilling and testing goal of the ladder/hurdle drill is for an athlete to minimize the time each foot spends on the ground at each step (i.e., "fast feet"). The acceleration data, as an indicator of the ground contact time for each foot during the ladder/hurdle drill, can be applied as a factor in an athleticism rating or as a guide to assist an athlete in improving ladder/hurdle drill skills. Likewise, such acceleration data can identify asymmetry in the ground contact time for the athlete's right and left feet. This asymmetry data can also be applied as a factor in an athleticism rating or as a guide to assist an athlete in improving the athlete's strength, speed and agility drill skills.

Step 310 is an optional additional step in method 300 and occurs during collection of the acceleration data. Step 310 indicates that the athlete is given real-time feedback as to whether the drill performance meets a predetermined performance criterion, such as whether the athlete's foot contact time is less than a predefined threshold foot contact time to satisfy a "fast feet" criterion. In one implementation, the predefined threshold foot contact time can be set or selected at athleticism rating processing device 106 (e.g., 0.25 sec). The real-time feedback can be audible or visual feedback provided by athleticism rating processing device 106 during the drill indicating whether the athlete's performance meets or fails to meet the threshold.

For example, an audible indicator could employ one tone to indicate that the criterion is being met, while a different tone indicates that the criterion is not being met. Likewise, a visual indicator could employ one color (e.g., green) to indicate that the criterion is being met, while a different color (e.g., red) indicates that the criterion is not being met. Such instantaneous and continuous feedback allows an athlete to modify performance during the drill. A coach could such feedback to test athlete performance in real time and also to set training goals for an athlete.

In addition, an average contact time for each foot can be calculated to determine whether one foot/leg is slower than the other. If one foot/leg is slower than the other, a coach could recommend or assign strength training and more attention on training drills to even the performance of both an athlete's feet or legs.

The ladder/hurdle drill of method 300 is described with reference to an athlete's performance over a generally flat surface. In another implementation, the data collection of method 300 may be applied to a step drill in which an athlete steps up to and down from one or more raised steps or platforms, such as a SPARQ Carlisle Speed BOX™ step drill platform available from SPARQ Marketing & Media of Portland, Oreg. The collection of acceleration data may be directed to counting step repetitions within fixed time and determining a foot contact time, as described above.

For example, step drill goals may include maximizing the number of foot strikes on the box or platform within a given time interval. In a drill version referred to as Step-Ups, the athlete steps quickly onto the box or platform with one foot and then, as soon as that foot lands on the box or platform, the other foot follows. The athlete then steps down in the same manner as quickly as possible. The goal is to minimize the number of steps in a given time interval such as by attempting to reduce the number of steps in subsequent drill sets. In addition to the number of foot strikes or steps, the amount of contact time can also be calculated and used in the manner described above. This can also be used for calculating athleticism ratings, improving athlete skills within the drill and as competition among various athletes.

As another example, multi-mode acceleration-based athleticism measurement system 100 can also be used in drills or tests that characterize stride length over a given distance, such as in sprints over a fixed distance (e.g., 40 yards).

Figure 4:
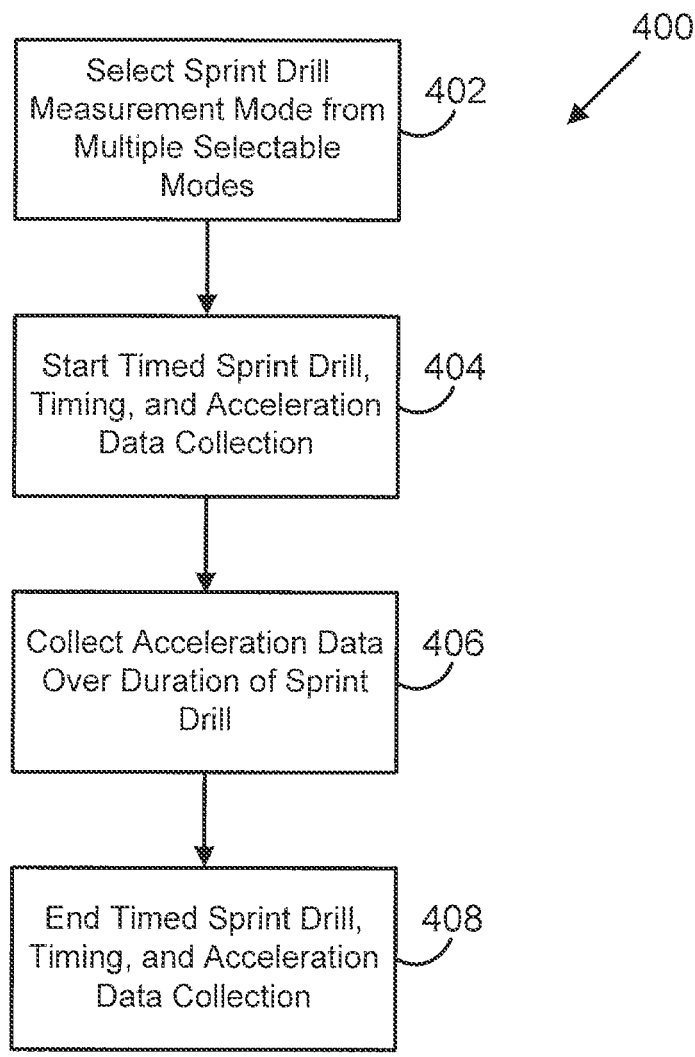
FIG. 4 is a flow diagram of a stride athletic performance measurement method as an illustration of another athleticism measurement mode according to the present invention.

FIG. 4 is a flow diagram of a stride athletic performance measurement method 400 that is performed during a fixed-distance sprint drill and may be used in connection with calculating an athletic performance rating or improving performance during sprint drills. In a fixed-distance sprint drill, an athlete runs as quickly as possible over the fixed distance. Conventionally, performance in a sprint drill is measured by measuring the overall time required for an athlete to run the fixed distance. The fixed-distance sprint athletic performance measurement may employ an acceleration sensor 102 positioned in or secured to one or each of the athlete's shoes, preferably an acceleration sensor 102 being positioned in or secured to each of the athlete's shoes.

In step 402 a sprint drill is selected from among multiple selectable drills or exercises, which correspond to different measurement modes, listed on athleticism rating processing device 106 that is worn or carried by the athlete.

In step 404 a timed sprint drill is started together with a start of timing of the overall drill duration and a start of collecting of acceleration data by athleticism measurement system 100 in a sprint drill mode. The acceleration data may be collected by athleticism rating processing device 106 that is worn or carried by the athlete. The start of timing of the overall drill duration may be initiated manually by an observer activating a timer or by the athlete crossing an optical timing start beam, and the start of collecting of acceleration data may be initiated by transmission of a wireless control signal to athleticism rating processing device 106 upon initiation of the overall timing.

In step 406 acceleration data are collected by athleticism measurement system 100 over the duration of the sprint drill.

In step 408 the timed sprint drill is ended together with timing of the overall drill duration and the collecting of acceleration data by athleticism measurement system 100. The timing of the overall drill duration may be ended manually by an observer de-activating a timer or by the athlete crossing an optical timing end beam, and the collecting of acceleration data may be ended by transmission of a wireless control signal to athleticism rating processing device 106 upon ending of the overall timing.

With an acceleration sensor 102 being positioned in or secured to each of the athlete's shoes, this acceleration data measurement mode can indicate the number of steps or strides over the fixed distance of the sprint drill. A drilling and testing goal of the sprint drill is for an athlete to minimize the number of steps or strides over the fixed-distance. The acceleration data, as an indicator of the number of steps or strides during a sprint drill, can be applied as a factor in using sprint drill results in an athleticism rating or as a guide to assist an athlete in improving sprint drill skills. For instance, a 40 yard sprint performed in 5.0 seconds with 20 strides may be performed in about 4.8 seconds with a lengthened stride that covers the distance in 19 strides. Moreover, acceleration data from both an athlete's shoes can identify asymmetry in the stride of an athlete's right and left legs. This asymmetry data can be applied as a factor in using sprint drill results in an athleticism rating or as a guide to assist an athlete in improving sprint drill skills.

It will be appreciated that in addition to determining stride length, as a number of strides over a fixed distance, the acceleration data in measurement method 400 can also indicate stride frequency and foot contact time. Moreover, the athlete may be given real-time feedback (e.g., audible) by athleticism rating processing device 106 during such a sprint drill. The feedback may indicate whether the athlete's performance meets or fails to meet a threshold stride frequency corresponding to a desired number of strides, or may cue the athlete with a cadence to a stride frequency. For example, in a 40 yard dash drill, audible feedback in the form of beeps or tones could initially have a relatively high frequency indicating quick acceleration strides and subsequently have al lower frequency corresponding to a longer, post-acceleration stride. At the end of the test or training drill, the athlete could review when the timing of his or her strides matched with the cued cadence and when it did not. Such cadence matching could be in addition to counting the total number of foot strikes and strides. Such data collection and feedback could be applied to other drills such as, for example, shuttle drills.

The measurement modes of agility athletic performance measurement method 300 and stride athletic performance measurement method 400 utilize each acceleration sensor 102 to measure acceleration generally along a vertical axis to detect foot strikes and associated performance characteristics. In another implementation, each acceleration sensor may measure acceleration along a lateral, generally horizontal axis to detect lateral changes in foot motion for measuring performance characteristics associated with an athlete changing direction from side-to-side. For example, such a vertical-lateral two-dimensional acceleration sensor 102 could be employed in athletic performance measurement method 300 to determine when an athlete changes direction relative foot placement to further characterize, or guide improvement in, performance of the drill. Also, the acceleration data in a lateral plan can be used to determine an agility or quickness rating. The two-dimensional acceleration data can be integrated over time to obtain velocity and a velocity vector to determine speed in linear and lateral dynamic movement, which can be applied in an athleticism rating of the athlete or guide the athlete toward improved performance in the particular drill.

As another example, multi-mode acceleration-based athleticism measurement system 100 with a vertical-lateral two-dimensional acceleration sensor 102 can be used in drills or tests that characterize direction-change reaction time in response to audible stimuli or commands.

Figure 5:
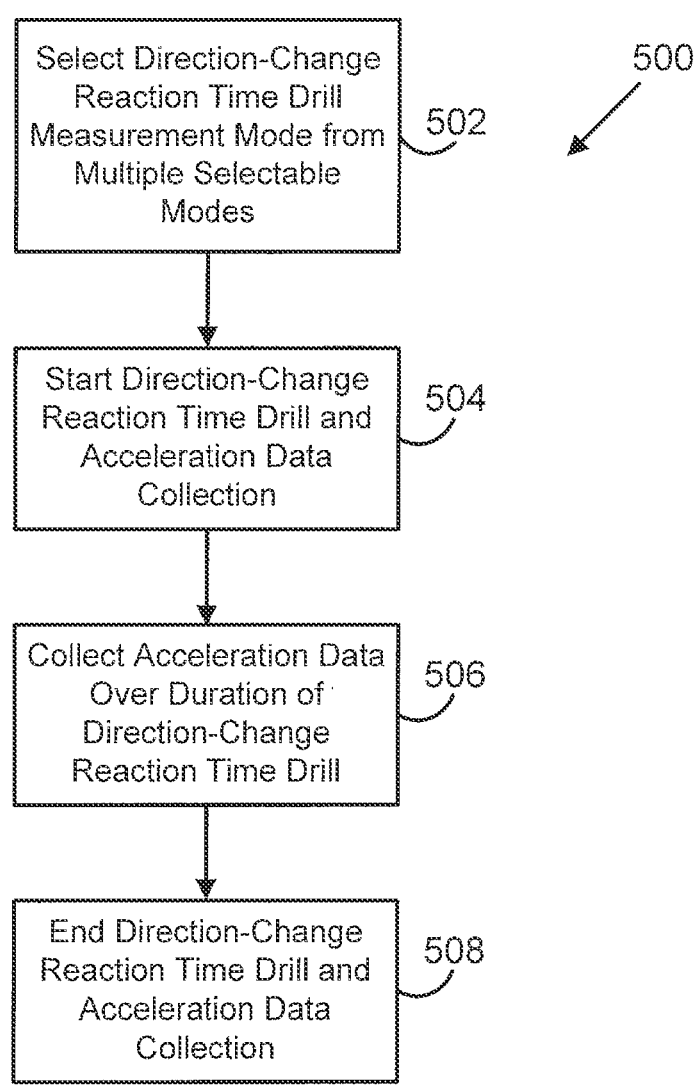
FIG. 5 is a flow diagram of a direction-change reaction time athletic performance measurement method as an illustration of yet another athleticism measurement mode according to the present invention.

FIG. 5 is a flow diagram of a direction-change reaction time athletic performance measurement method 500 that is performed as a direction-change reaction time drill over a selected number of samples and may be used in connection with calculating an athletic performance rating or improving performance during such reaction time drills. In a direction-change reaction time drill, an athlete changes lateral direction as quickly as possible in responses to triggers or commands, which may be provided audibly or visible. The following description is made with reference to audible triggers, but is similarly applicable to visible triggers. The direction-change reaction time athletic performance measurement may employ a vertical-lateral two-dimensional acceleration sensor 102 positioned in or secured to one or each of the athlete's shoes, preferably an acceleration sensor 102 being positioned in or secured to each of the athlete's shoes. Conventionally, direction-change reaction time drills are simply exercises and are not measured for lack of an available measurement device.

In step 502 a direction-change reaction time drill is selected from among multiple selectable drills or exercises, which correspond to different measurement modes, listed on athleticism rating processing device 106 that is worn or carried by the athlete.

In step 504 a direction-change reaction time drill is started together with a start of collecting of acceleration data by athleticism measurement system 100 in a direction-change reaction time drill mode. The acceleration data may be collected by athleticism rating processing device 106 that is worn or carried by the athlete. The start of collecting of acceleration data may be initiated by an audible cue generated by the athleticism rating processing device 106. In one implementation, the audible cue may be a simple tone or beep in response to which the athlete is to take a lateral step in a direction opposite of any prior lateral step. In another implementation, the audible cue may be a verbal instruction to take a lateral step in a specified direction. Preferably, the start of collecting of acceleration data begins after an audible warning that the drill is about to begin.

In step 506 acceleration data are collected by athleticism measurement system 100 over the duration of the direction-change reaction time drill.

In step 508 the direction-change reaction time drill is ended by an audible termination cue together with ending of the collecting of acceleration data by athleticism measurement system 100 based on a selected number or sequence of audible cues.

With a vertical-lateral two-dimensional acceleration sensor 102 being positioned in or secured to each of the athlete's shoes, the acceleration data measurement mode indicates the time duration between each audible cue and the resulting lateral step of the athlete, thereby measuring a lateral change of direction reaction time in response to each audible cue. A drilling and testing goal of the direction-change reaction time drill is for an athlete to minimize reaction time in response to a cue or stimulus. The acceleration data, as an indicator of the reaction time during the drill, can be applied as a factor in an athleticism rating calculation or as a guide to assist an athlete in improving direction-change reaction time skills.

Direction-change reaction time athletic performance measurement method 500 is described with reference to a vertical-lateral two-dimensional acceleration sensor 102. It will be appreciated that in other implementations acceleration sensor 102 may sense acceleration along vertical and axial axes and be used in a direction-change reaction time athletic performance measurement directed to forward and backward changes of direction. Alternatively, acceleration sensor 102 may sense acceleration along vertical, lateral, and axial axes and be used in a direction-change reaction time athletic performance measurement directed to lateral changes of direction as well as forward and backward changes of direction.

As another example, multi-mode acceleration-based athleticism measurement system 100 with a two-dimensional acceleration sensor 102 secured to one or each of an athlete's wrists, in addition to an acceleration sensor secured to one or both of the athlete's shoes, can be used in drills or tests that characterize directions of arm movement during running relative to running stride information. For example, a two-dimensional acceleration sensor 102 on each wrist can be used to determine and measure arm movement to characterize or guide improvement in the arm movement.

The arms have two main functions when running—developing a source of power and counter-acting unwanted rotation produced by running. An athlete's arm speed can increase overall running speed when the arm speed and motion are executed properly. In one characterization, proper arm movement includes forward movement extending the hands higher than the shoulders and backward movement extending hands behind the hips, all while the elbows are bent at 90-degrees and the hands do not cross the body bilateral centerline. At the moment of each foot strike, the opposite-side arm should be in front and starting to move back behind the hips. The change in direction of the arm will correspond to a change in direction of acceleration on the wrist-borne acceleration sensor 102.

Athlete arm movement performance information from wrist-borne acceleration sensors 102 may be collected together with running stride information collected from shoe-mounted sensors 102. The arm movement data may be used to characterize or guide improvement of an athlete's performance, either during a drill directed solely to measuring arm movement or during a drill that measures arm movement as well as stride or other information, such as information about synchronization of arm movement with foot strikes and stride. Arm movement characterizations may be based upon on samples of athletes of different heights running at different speeds to correlate the measured hand movement to a preferred full-range arm motion to guide athletes away from undesired short, fast arm movements. Moreover, real-time feedback can be applied to arm movement range or arm movement synchronization during a performance drill.

It will be appreciated that the measurement modes described with reference to FIGS. 2-5 are examples of multiple measurement modes in which multi-mode acceleration-based athleticism measurement system 100 can be used. Examples measurement modes in which multi-mode acceleration-based athleticism measurement system 100 can be used include stride frequency (Hz), flight time (per stride of average over time), maximum acceleration, maximum velocity, etc. Based on sample gait data for different velocities, from walking to running to sprinting, a stride length can be concluded from the acceleration data. Once a stride length is calculated, distance can be calculated from the foot strikes indicated by peak-to-peak acceleration data. In addition, a running average of velocity and acceleration can be computed to determine maximum acceleration and velocity during a training test or drill.

As another example, athleticism measurement system 100 can be used to determine athlete power based upon "explosiveness" of a first step movement. In this mode, acceleration data obtained during a vertical jump drill can directly indicate an athlete's loft time, from which a vertical height of the jump can be directly calculated, together with the forcefulness or power based upon the athlete's weight.

As yet another example, once the velocity curve over time is calculated, an area under the curve or a differential of a velocity over time curve can be used to determine an athlete's power expenditure. An athlete's maximum power can be calculated with respect to a maximum velocity as an upper limit. Similarly, a true power rating of athletic work performed can be expressed in watts (W).

In view of the many possible embodiments to which the principles of this invention may be applied, it should be recognized that the detailed embodiments are illustrative only and should not be taken as limiting the scope of our invention. Rather, the invention includes all such embodiments as may come within the scope and spirit of the following claims and equivalents thereto.

What is claimed is:

1. An apparatus comprising:
   a user input device;
   a sensor;
   a processor; and
   memory storing computer readable instructions that, when executed by the processor, cause the processor to at least:
   track movement of the sensor, wherein data from the movement of the sensor is recognized as a user's physical activity, and wherein the data includes an average contact time for each foot of the user and indicates whether one leg of the user is slower than the other;
   compare the data to a predetermined performance criterion; and
   electronically transmit a guide for improving a running movement efficiency of the user based on the comparison of the data to the predetermined performance criterion, wherein the guide for improving running movement efficiency is calculated by analyzing acceleration data associated with at least one of the user's wrists and at least one of the user's shoes to characterize directions of arm movement during running relative to running stride information.

2. The apparatus of claim 1, wherein the predetermined performance criterion includes a foot contact time threshold that satisfies a fast feet criterion.

3. The apparatus of claim 1, wherein the predetermined performance criterion includes an accuracy threshold of a user's movement.

4. The apparatus of claim 1, wherein the predetermined performance criterion includes a quantity threshold of user movement.

5. The apparatus of claim 1, wherein the guide comprises feedback electronically transmitted in real-time.

6. The apparatus of claim 1, wherein the guide includes coaching recommendations for improvement based on the comparison of the physical activity data to the predetermined performance criterion.

7. The apparatus of claim 1, wherein the predetermined performance criterion includes one or more cues for performing an action, based on the comparison of the physical activity data to the predetermined performance criterion.

8. The apparatus of claim 1, wherein the apparatus further comprises at least one wrist worn sensor.

9. A non-transitory computer readable medium storing instructions that, when executed by a processor of an apparatus, cause the processor of the apparatus to:
   track movement of a sensor, wherein data from the movement of the sensor is recognized as a user's physical activity, and wherein the data includes an average contact time for each foot of the user and indicates whether one leg of the user is slower than the other;
   compare the data to a predetermined performance criterion; and
   electronically providing a guide for improving running movement efficiency of the user based on the comparison of the physical activity data to the predetermined performance criterion.

10. The non-transitory computer readable medium of claim 9, wherein the predetermined performance criterion includes a foot contact time threshold that satisfies a fast feet criterion.

11. The non-transitory computer readable medium of claim 9, wherein the predetermined performance criterion includes an accuracy threshold of a user's movement.

12. The non-transitory computer readable medium of claim 9, wherein the predetermined performance criterion includes a quantity threshold of user movement.

13. The non-transitory computer readable medium of claim 9, wherein the guide comprises electronically-transmitted feedback provided in real-time.

14. The non-transitory computer readable medium of claim 9, wherein the guide includes coaching recommendations for improvement that are based on the comparison of the data to the predetermined performance criterion.

15. The non-transitory computer readable medium of claim 9, wherein the predetermined performance criterion includes one or more cues for performing an action that are based on the comparison of the physical activity data to the predetermined performance criterion.

16. The non-transitory computer readable medium of claim 9, wherein determining the physical activity data corresponding to the user's physical activity includes receiving data from at least one wrist worn sensor.

17. The non-transitory computer readable medium of claim 9, wherein determining the physical activity data corresponding to the user's physical activity includes receiving data from at least one appendage worn sensor.

18. The non-transitory computer readable medium of claim 9, wherein the tracking of the movement of the sensor comprises receiving an electronic signal from an accelerometer.

19. The non-transitory computer readable medium of claim 9, wherein the electronically providing the guide comprises transmitting the guide over a wireless communication protocol.

20. An apparatus comprising:
    a user input device;
    a sensor;
    a processor; and
    memory storing computer readable instructions that, when executed by the processor, cause the processor to at least:

track movement of the sensor, wherein data from the movement of the sensor is recognized as a user's physical activity, and wherein the data includes an average contact time for each foot of the user and indicates whether one leg of the user is slower than the other;

compare the data to a predetermined performance criterion; and electronically transmit a guide for improving a running movement efficiency of the user based on the comparison of the data to the predetermined performance criterion, wherein the guide for improving running movement efficiency is calculated by analyzing acceleration data associated with at least one of the user's shoes to characterize running stride information.

* * * * *